United States Patent [19]
Douglass

[11] Patent Number: 5,542,849
[45] Date of Patent: Aug. 6, 1996

[54] SYSTEM FOR SELF-TYPING OF INDIVIDUAL ESSENCES

[76] Inventor: Milo R. Douglass, P.O. Box 1210, Kapaa, Hi. 96746

[21] Appl. No.: 374,465
[22] Filed: Jan. 18, 1995
[51] Int. Cl.⁶ .................................................. G09B 1/00
[52] U.S. Cl. .................................. 434/236; 434/322
[58] Field of Search .................................. 434/236, 345, 434/346, 343, 322, 433, 99

[56] References Cited

U.S. PATENT DOCUMENTS

| | | |
|---|---|---|
| 1,582,122 | 4/1926 | Clapp. |
| 2,959,871 | 11/1960 | Hunkavaara ........................... 434/236 |
| 3,491,196 | 1/1970 | Stein ........................................ 434/345 |
| 3,755,921 | 9/1973 | Heller ...................................... 434/322 |
| 3,811,203 | 6/1974 | Mayfield ................................. 434/236 |
| 4,173,833 | 11/1979 | Rosenblatt ............................. 434/236 |
| 4,241,738 | 12/1980 | Lubbers et al. . |
| 4,561,850 | 12/1985 | Fabbri; et al. . |
| 4,654,794 | 3/1987 | O'Brien . |
| 4,975,060 | 12/1990 | Rosetti .................................... 434/236 |
| 5,190,458 | 3/1993 | Driesener ............................... 434/236 |

OTHER PUBLICATIONS

Jackson, Carole, *Color Me Beautiful* 1973, pp. 25–59.
Pinckney, Gerrie and Swanson, Marge, *Your New Image Through Color and Line*, 1981, pp.
Kentner, Bernice, *A Rainbow in Your Eyes*, 1981, pp. 10–19.
Eiseman, Leatrice, *Alive with Color*, 1983, pp. 8–27.
Luscher, Max, *The Luscher Color Test*, 1969, pp. 11–27.
Pooser, Doris, *Always In Style*, 1989, pp. 26–144.
Callaway, Joan, *The Color Connection: From a Retailer's Perspective*, 1986, pp. 27–33.
Caygill, Suzanne, *COLOR The Essence of You*, 1980, pp. 151–163.
Segerstrom, Jane, Look Like Yourself & Love It!, 1980, pp. 15–25.
Cho, Emily, et al. *It's You!*, 1986, pp. 2–15.
Jackson, Carole, *Color for Men*, 1984, Chapter 4, pp. 43–57.
Itten, Johannes, *The Art of Color*, 1961, pp. 24–32.
Fujii, Donna, Color with Style, Misc. pages.
Cass Hogan, Lee and Anderson, Karen E., *Look Like a Winner!*, 1985, pp. 9–22.

*Primary Examiner*—Paul J. Hirsch
*Attorney, Agent, or Firm*—Patterson & Keough, P.A.

[57] ABSTRACT

A system for self-typing of individual essences recognizes that particular characteristic archetypes of individuals resonate with particular characteristic types of sensory stimuli and tests for responses to a set of sensory stimuli in a way in which the individual is unaware of any relationship between each of the sensory stimuli and the particular characteristic archetype associated with that sensory stimuli. Because the relation between each sensory stimuli and its characteristic archetype is unknown to the individual, the self-test system removes the subjective ego of the individual from the evaluation. As a result, even though the self-test system is relatively simple to administer, the accuracy of the self-test system is greatly enhanced.

26 Claims, 4 Drawing Sheets

SYSTEM FOR SELF-TYPING OF INDIVIDUAL ESSENCES

TECHNICAL FIELD

The present invention relates generally to systems for testing and typing individuals. More particularly, the present invention relates to a system for self-typing of individual essences or inherent characteristic archetypes in reaction to sensory stimuli.

BACKGROUND OF THE INVENTION

It has long been known that different people respond differently to different sensory stimuli. In the fashion industry, for example, it is accepted that a person will look good in certain colors or fabrics, but will be unable to wear other colors or fabrics. In the use of aromatics, it is known that some people will respond favorably to a particular scent, while others will react unfavorably to the same scent. In cosmetics, different tones and shades of colors are used to evoke different kinds of moods. Similarly different visual patterns will produce different reactions when viewed by different individuals. Different people will even respond differently to the feel of different textures and fabrics.

Although it is commonly understood that different individuals will have different reactions to sensory stimuli, there have only been a few attempts to systematically categorize the reactions of different groups of individuals to different sensory stimuli. The possibility that there are distinct categorizations of the coloring and skin tones of individuals was first recognized by the artist Joseph Itten in the early part of the 20th century. Itten, J., *The Art of Color*, Van Nostrand Reinhold, New York, N.Y. (1973). Perhaps the most well-known system for color categorization is the four-season theory of color and fashion originally developed in the 1950's and 60's by Suzanne Caygill and later popularized by Carole Jackson. Caygill, S., *Color: The Essence of You*, Celestial Arts, Millbrae, Calif. (1981). Jackson, C., *Color Me Beautiful*, Acropolis Books, Washington, D.C. (1973), and *Color for Men*, Ballantine Books, New York, New York (1984). In the four-season color theory, a match is made between a characteristic base color of a person's skin tone and a certain group of colors and styles which look best when worn by that person. The colors and styles are grouped according to the different seasons: spring, summer, fall and winter.

One of the advantages of color matching techniques such as the four-season color theory is the ability to categorize an individual as a member of a larger class of individuals who have similar types of characteristics. Philosophers and psychologists from as early as Hippocrates have recognized that people can be generally classified as having a predominate set of personality characteristics. Interestingly, most of these types of classifications schemes which have been proposed throughout history break down personality characteristics into four broad categories which have often been referred to as archetypes, such as Sanguine, Phlegmatic, Choleric and Melancholic as defined by Hippocrates; King, Lover, Warrior and Magician as defined by Robert Moore and Douglas Gillette, and Expressive, Amiable, Driver, Analytical as defined by Wilson Learning Corporation. Other well-known historic characteristic archetype classification systems include the six Chinese personality characteristics: Yin/Yang, Dramatic, Natural, Gamin/Classic, Romantic, and Ingenue; and the three Ayruvedic body/personality types: Kaffa, Vatta and Pita.

Understanding the nature of each of these broad categories of personality characteristic classifications or archetypes offers the possibility for enhanced personal insight and awareness. As psychologists have come to appreciate, however, the challenge in realizing any value from an understanding of an individual's archetype is intimately bound up with the ability to properly categorize that individual into one of the archetypes. Because human beings are complex and highly adaptable creatures, there is often a tendency for individuals to act out of an archetype that is more often dictated by an individual's personal experiences and family of origin, rather than out of an archetype which is inherent for that individual. It is apparent that the process of determining an individual's inherent archetype by reference to his or her personality characteristics is far from an objective process.

If there is a relationship between personality archetypes and an individual's response to sensory stimuli, then the ability to "type" that individual by his or her characteristic response to sensory stimuli has the potential to offer unique insights into the inherent archetype or individual essence of that person. The problem is that most techniques for characterizing the physical attributes and responses of an individual are as subjective in their evaluation of an individual's characteristics responses to sensory stimuli as any subjective analysis of that individual's personality characteristics. Systems, such as the four-season color theory, offer no systematic objective way of testing or typing an individual to determine what season of colors best matches that individual.

Typing for the four-season color theory is done either by a professional color consultant skilled in color theory in a one-on-one session, or by an individual using subjective recollection and reaction to particular groups of colors as part of a self-match test. In the former case, typing is an individual and expensive process that requires the trained skills of a professional color consultant. The color consultant renders a subjective analysis based on observations of that person which is very similar to a subjective personality evaluation which would be performed by a psychologist of psychiatrist. In the later case, the subjective reactions of the individual may alter or skew the results of the typing.

With proper training and sufficient time, a color evaluation performed by a professional color can be accurate and is the only way which some proponents of the four-season theory of color recommend that typing be performed. Callaway, J., *The Color Connection: From a Retailer's Perspective*, Winterspring Press, Davis, Calif. (1986). Unfortunately, there are few formal programs to train color consultants and no recognized standards by which to evaluate the accuracy of this kind of professional typing.

The time and expense involved in on one-on-one professional color consultation sessions has lead to the development of several self-matching tests that, without the benefit of any training in color analysis, ask individuals to match their hair, skin and eye colors with a series of colored swatches in order to determine their own color season or type. There are several other versions of the type of self-matching tests described by Caygill and Jackson which rely solely on a self-matching of colors. Mumford, J., *Everyone is Someone in Color*, Publishers Press, Salt Lake City, Utah (1976); Elseman, L., *Alive with Color*; and *Color Works*, video by Color One Institute. Another kind of self-match test that does not attempt to classify individuals according to a characteristic type is U.S. Pat. No. 5,178,169 issued to Lamle which describes a cosmetics selecting device that is a flexible strip having different color, shade and tones of cosmetics which is placed across the forehead to allow a user to select which color, shade and tone best matches the individuals skin color. Obviously, the problems of inaccuracy in typing by strict color matching are greatly compounded by any of these kinds of self-matching tests where the tests are attempted by someone without formal color training.

In an attempt to rely less on strict color matching, several existing self-test systems combine a subjective analysis of color matching with a subjective analysis of personality characteristics in order to type individuals. Kentner, B., *Color Me a Season, How to Find and Use Your Most Flattering Colors,* KenKra Publishers, Concord, Calif. (1978); Segerstrom, J., *Look Like Yourself & Love It!,* Triad Press, Houston, Tex. (1980); Kentner, B., *A Rainbow in Your Eyes,* KenKra Publishers, Concord, Calif. (1981); Pickney, G. and Swenson, M., *Your New Image Through Color and Line,* Fashion Image/Crown Summit Books, Costa Mesa, Calif. (1981). While the idea of using a psychological evaluation to assist in self-typing would seem to provide better results in terms of accuracy, the accuracy of these combined self-test system is often less than that of color matching alone. This can be understood by realizing that instead of having one subjective test administered by a non-professional, these systems use two subjective tests that are self-administered.

Other systems have been proposed to solve the inaccuracy problems which are associated with color typing through subjective color matching. U.S. Pat. No. 4,681,546 issued to Hart describes a method of spectrum analysis of the natural tones of the person's skin by using a color filter system to determine the distribution and concentration of primary colors, and then categorizing wearing apparel and accessories into classes based on concentrations of the primary colors in those articles. U.S. Pat. Nos. 5,311,293, 5,313,267 and 4,969,632 issued to McFarlane et al. describe methods and instruments for identifying skin color categories based upon blue and yellow undertones of the skin as measured by a color measuring device. As with color typing by professional color consultants, these systems are expensive and can require sophisticated equipment in order to perform a color analysis. More importantly, these systems are limited to the accuracy of the color analysis, which at present is less accurate than human color perception. In addition, these systems cannot analyze differences in sensory stimuli other than pure color matching.

Although the possibility of typing individuals by their characteristic response to sensory stimuli has tremendous potential, existing techniques and systems for performing such typing have significant limitations that preclude their widespread use. Accordingly, it would be desirable to provide a system for characteristic typing of individual essences in reaction to sensory stimuli which overcomes the limitations of existing techniques and system and which allows for widespread use of this information.

SUMMARY OF THE INVENTION

The present invention is a system for self-typing of individual essences which recognizes that particular characteristic archetypes of individuals resonate with particular characteristic types of sensory stimuli and tests for responses to a set of sensory stimuli in a way in which the individual is unaware of any relationship between each of the sensory stimuli and the particular characteristic archetype associated with that sensory stimuli. Because the relation between each sensory stimuli and its characteristic archetype is unknown to the individual, the self-typing system removes the subjective ego of the individual from the evaluation. As a result, even though the self-typing system is relatively simple to administer, the accuracy of the self-typing system is greatly enhanced.

In accordance with a first aspect of the present invention, a method for self-typing of an inherent characteristic archetype that is an essence of an individual comprises the steps of providing the individual with at least four sensory stimuli. Each sensory stimuli has a relation with only one of at least four characteristic archetypes, that relation between each sensory stimuli and its characteristic archetype being unknown to the individual. Next, the individual observes at least one perception in response to a sensory reaction for each of the at least four sensory stimuli. Based upon these perceptions, the individual selects one of the at least four sensory stimuli as the inherent characteristic archetype that represents the essence of that individual.

In accordance with a second aspect of the present invention, a system for self-typing an inherent characteristic archetype that is an essence of an individual comprises at least four sensory stimuli and a set of instructions presented to the individual. Each sensory stimuli has a relation with only one of at least four characteristic archetypes, that relation between each sensory stimuli and its characteristic archetype being unknown to the individual. The set of instruction directs the individual to observe at least one perception in response to a sensory reaction for each of the at least four sensory stimuli. In response, the individual selects one of the at least four sensory stimuli as the inherent characteristic archetype representing the essence of that individual.

Preferably, more than one question is asked of the individual so that multiple perceptions in response to the sensory stimuli are evoked where at least one of the questions is a placebo question that is not utilized to make a determination of the inherent characteristic archetype representing the essence of that individual. It has been found that if a question evokes a comparison of likes, the response to the sensory stimuli is more likely to be based on an ego response that can distort the results of the self-test; whereas if the question evokes a comparison of harmonization with each of the sensory stimuli, the response to the sensory stimuli is more likely to be based on a non-ego response that more accurately reflects the inherent characteristic archetype representing the essence of that individual. The questions which are posed to the individuals can be presented as written material, video material, or audio material, or any combination thereof. It is also possible to confirm the one of the at least four sensory stimuli selected as the inherent characteristic archetype by repeating the self-test with at least one different set of at least four sensory stimuli.

The sensory stimuli may comprise a smell, a taste, a sound, a shape, a pattern, a texture, a color, or any combination thereof. Preferably, the sensory stimuli are four forms, each form having a unique shape, a unique color, and a unique surface texture that is visual compared to the individual. Alternatively, the sensory stimuli may be four scents, four sample tastes or four sample sounds, each having a unique smell, taste or combination of tones that is compared by the individual. In another alternative, the sensory stimuli are four harmonic family sets. Each harmonic family set has a series of sample representations, each sample representation having a unique color, a unique design and a unique texture and all of the sample representations for each set presenting a harmonic family of visually perceived energetic patterns that is associated with only one of at least four characteristic archetypes.

In accordance with a preferred embodiment of the present invention, a set of four sensory stimuli for use in typing an inherent characteristic archetype will include a first sensory stimuli comprised of a circular shape having a surface texture that is natural and semi-gloss and a color tint that is a pale yellow, a second sensory stimuli comprised of a tear-drop shape having a surface texture that is smooth and velvety and a color tint that is a pale rose, a third sensory stimuli comprised of a triangular shape having a surface texture that is rough and course and a color tint that is a pale brown, and a fourth sensory stimuli comprised of an oval shape having a surface texture that is hard, glossy and shiny and a color tint that is a pure white. All of the sensory stimuli will be of a size that may hand-held. Each stimuli may constructed either solely from paperboard stock matching the desired physical characteristics, or from pieces of fabric material matching the desired physical characteristics that are adhered to a rigid backing.

In accordance with an alternate preferred embodiment of the present invention, an arrangement of a set of four sensory stimuli for use in typing an inherent characteristic archetype comprises four groups or family of swatches of both color and designs: a first family of vibrant color swatches having light, curved, chaotic and upward-directed designs; a-second family of muted color swatches having smooth, curved, flowing and downward-directed designs; a third family of earth-tone color swatches having staccato, straight, asymmetric and upward-directed designs; and a fourth family of intense color swatches having still, straight or curved, symmetric and downward-directed designs. The arrangement may comprise either a circular arrangement wherein each of the four families are presented within a unique quarter circle or a circular shape, or a strip arrangement wherein each of the four families in are presented as individual strips.

DETAILED DESCRIPTION OF THE PREFERRED EMBODIMENTS

Figure 1:
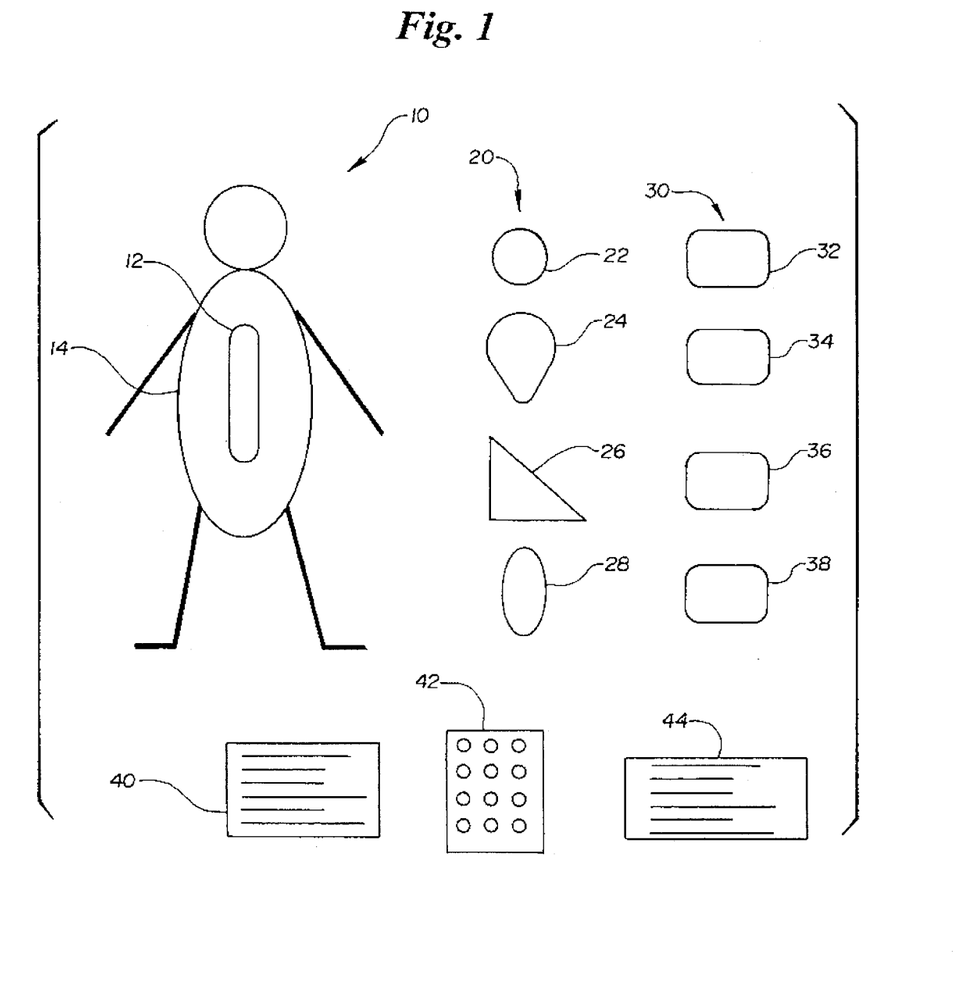
FIG. 1 is an overall block diagram of the self-typing system of the present invention.

Referring now to FIG. 1, an overall block diagram is shown of a self-typing system 10 in accordance with the present invention. Self-typing system 10 is utilized to access or "type" an inherent characteristic archetype or essence 12 of an individual 14. For purposes of the present invention, archetype is defined as a broad categorization of people who share common characteristics or attributes. As previously discussed in the Background Section, there are many archetypal categorizations which have been defined throughout history. Although the reasons why archetypal categorizations have general validity are not well understood, it is commonly accepted that people tend to exhibit the characteristics of one or more of these archetypal categories. Because human beings are highly adaptable creatures, it is sometimes very difficult to accurately identify the true characteristic nature or essence 12 of an individual 14 based only on the characteristics which that persons tends to exhibit. Self-typing system 10 avoids the problems of existing techniques for categorizing people by accessing the true characteristic archetype or essence in a way that removes the ego of individual 14 from the evaluation. As a result, even though self-typing system 10 is relatively simple to administer, the accuracy of self-typing system 10 is greatly enhanced.

Self-typing system 10 includes a set 20 of least four sensory stimuli 22, 24, 26 and 28. Each sensory stimuli 22, 24, 26 and 28 has a relation with only one of at least four characteristic archetypes; however, the relation between each sensory stimuli 22, 24, 26 and 28 and its characteristic archetype is unknown to individual 14. A set of instructions 42 110 directs individual 14 to observe at least one perception in response to a sensory reaction for each of sensory stimuli 22, 24, 26 and 28 of set 20. In response, individual 14 selects one sensory stimuli 22, 24, 26 and 28 from set 20 which, unknown to individual 14, is the inherent characteristic archetype representing the true essence 12 of individual 14. In an alternate embodiment of self-typing system 10, at least two different sets 20 and 30 of at least four sensory stimuli 22, 24, 26 and 28 and 32, 34, 36 and 38 are used to elicit a sensory reaction of individual 14. In this embodiment, instructions 40 direct individual 14 to observe at least one perception in response to a sensory reaction for each different set 20, 30. The one of sensory stimuli 22, 24, 26 and 28 and the one of sensory stimuli 32, 34, 36 and 38 which are selected by individual 14 in response to each different set 20 and 30 are compared to confirm the accuracy of the identification of the inherent characteristic archetype or essence 12.

Figure 2:
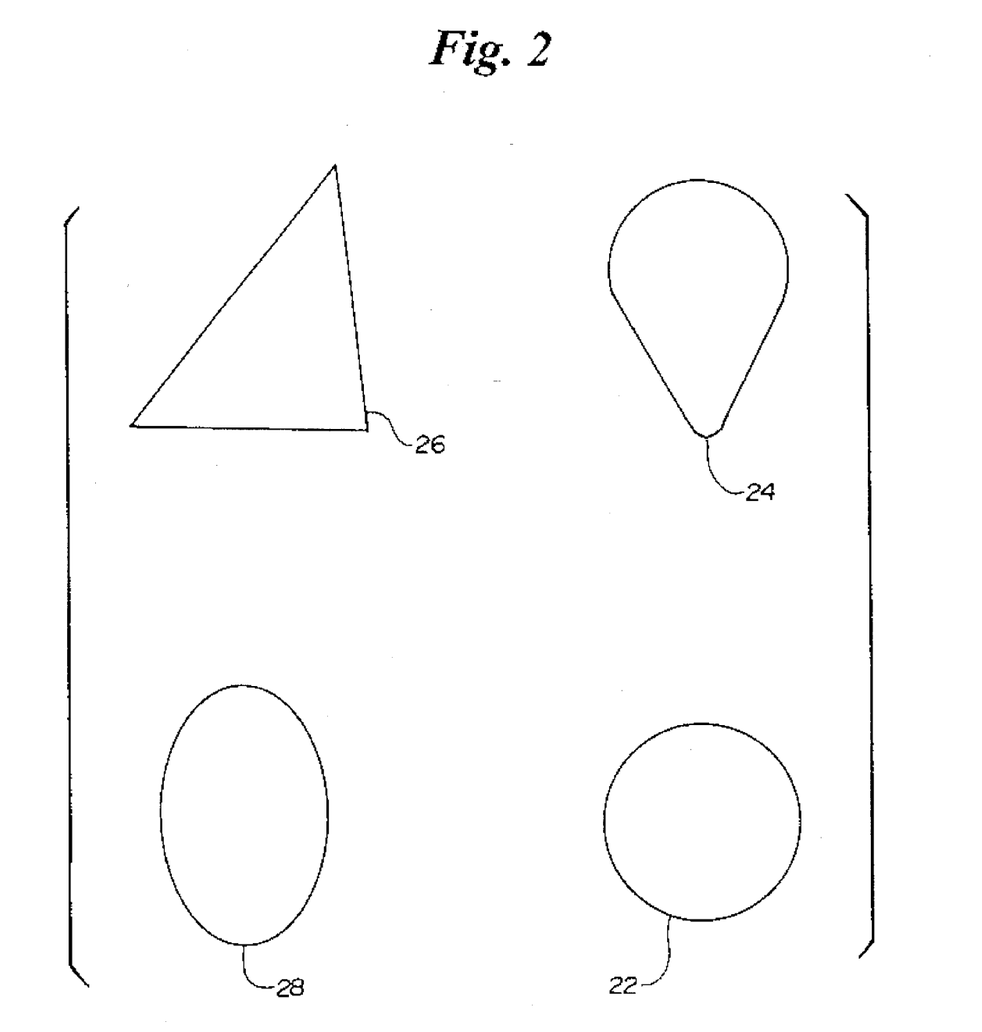
FIG. 2 is a more detailed representation of one set of sensory stimuli in accordance with a preferred embodiment of the present invention.

Referring now to FIG. 2, a preferred embodiment of first set 20 of sensory stimuli will be described. As can be seen in FIG. 2, each stimuli 22, 24, 26 and 28 is a different and unique shape. In a preferred embodiment, stimuli 22 is a circle shape and generally corresponds with Type I archetypes, such as Sanguine, Magician, Expressive, and Spring. Stimuli 24 is a teardrop shape and generally corresponds with Type II archetypes, such as Phlegmatic, Lover, Amiable and Summer. Stimuli 26 is a triangular shape and generally corresponds with Type III archetypes, such as Choleric, Warrior, Driver and Autumn. Stimuli 28 is an oval shape and generally corresponds with Type IV archetypes, such as Melancholy, King, Analytical and Winter.

In a preferred embodiment shown in FIG. 2, in addition to shape, each stimuli is also provided with a unique surface texture and a unique color tint. For stimuli 22 corresponding to Type I archetypes, the surface texture is natural and semi-gloss, and the color tint is a pale yellow. For stimuli 24 corresponding to Type II archetypes, the surface texture is smooth and velvety, and the color tint is a pale rose. For stimuli 26 corresponding to Type III archetypes, the surface texture is rough and course, and the color tint is a pale brown. For stimuli 28 corresponding to Type IV archetypes, the surface texture is hard, glossy and shiny, and the color tint is a pure white.

In one embodiment, stimuli 22, 24, 26 and 28 are constructed solely from paperboard stock matching the desired physical characteristics. In another embodiment, stimuli 22, 24, 26 and 28 are comprised of pieces of fabric material matching the desired physical characteristics that are adhered to a rigid backing, such as cardboard. The size of stimuli 22, 24, 26 and 28 is preferably such that individual 14 can easily manipulate these stimuli by hand.

Figure 3:
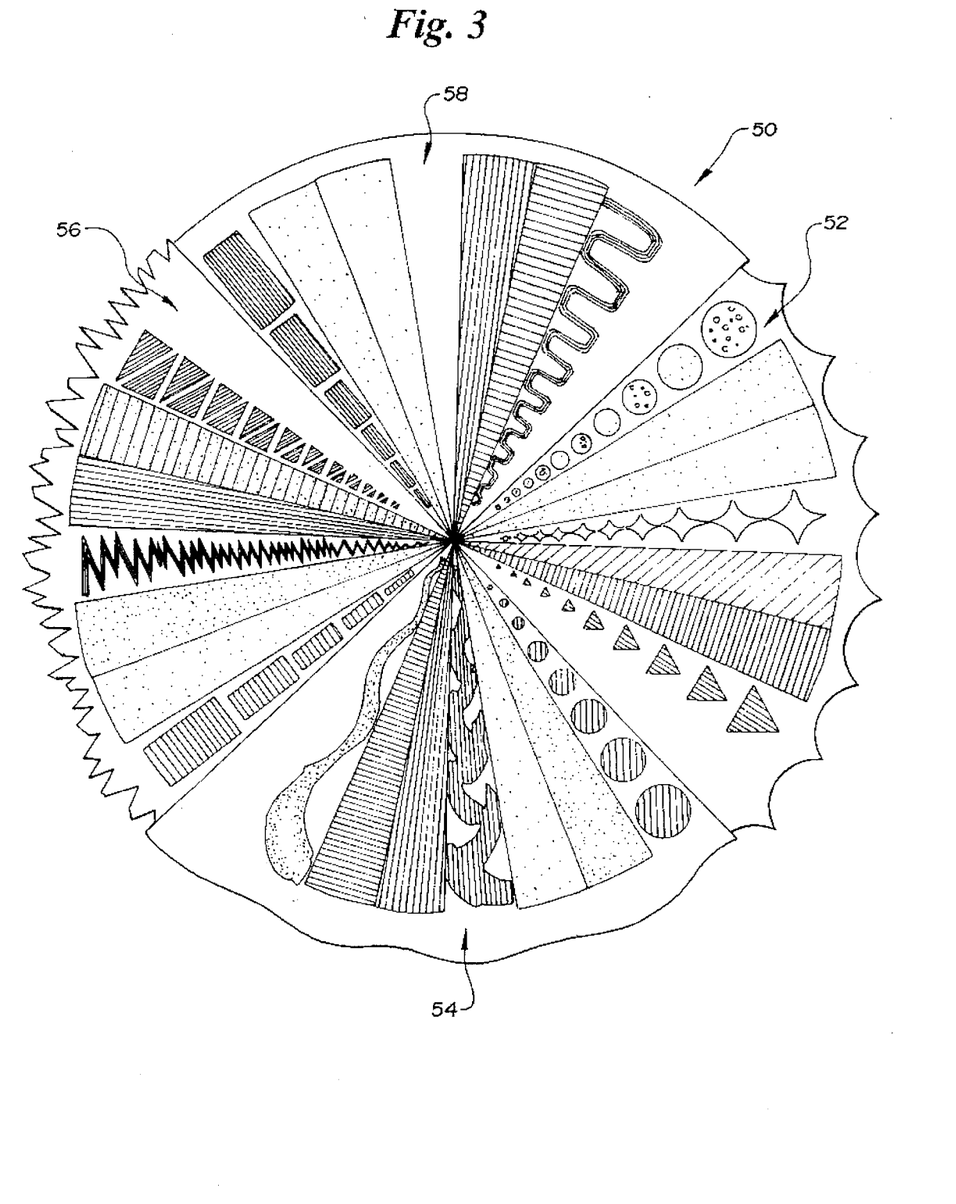
FIG. 3 is a more detailed representation of another set of sensory stimuli in accordance with an alternate embodiment of the present invention.

In an alternate embodiment shown in FIG. 3, each stimuli 32, 34, 36 and 38 is comprised of a group or family of swatches 50 of both color and designs. Stimuli 32 corresponding to Type I archetypes includes a family of vibrant color swatches 52 having light, curved, chaotic and upward-directed designs. Stimuli 34 corresponding to Type II archetypes includes a family of muted color swatches 54 having smooth, curved, flowing and downward-directed designs. Stimuli 36 corresponding to Type III archetypes includes a family of earth-tone color swatches 56 having staccato, straight, asymmetric and upward-directed designs. Stimuli 38 corresponding to Type IV archetypes includes a family of intense color swatches 58 having still, straight or curved, symmetric and downward-directed designs.

The arrangement of energetic families 52, 54, 56 and 58 is a circular arrangement wherein each of the four families are presented within a unique quarter circle or a circular shape. Alternatively, a strip arrangement of energetic families 52, 54, 56 and 58 could be used wherein each of the four families are presented as individual strips of swatches. It will be recognized that many variations of the arrangement of the energetic familes 52, 54, 56 and 58, or the particular individual swatches within any one energetic family could be made and still be within the scope of the present invention.

In both of the embodiments shown in FIGS. 2 and 3, there is no directly perceivable relationship between the corresponding archetypes and the physically perceivable characteristics of each stimuli. Without knowing the relationships between stimuli 22, 24, 26 and 28 and each corresponding archetype, even a familiarity with the personality characteristics of each of the archetypes, for example, does not provide individual 14 with any definite perception of which shape is associated with which archetype. This is because there is no general awareness or preconceived relationship between shape and archetypes. A similar statement can be made for the subtle texture and color tint of each stimuli which are included in the preferred embodiment of sensory set 20. Because stimuli 32, 34, 36 and 38 of sensory set 30 contain more perceivable information, it will be apparent that the chance of individual 14 discerning a relationship between these stimuli and the corresponding archetypes is increased. In the general population, however, there is still little chance of an individual 14 having sufficient knowledge of these relationships to significantly bias the results of self-test system 10.

Other stimuli which could be substituted for sensory sets 20 and 30 would include a set of four unique smells, four unique tastes, four unique textures or four unique sounds. In each of these cases, the sensory perception which individual 14 would be asked to observe would be smell, taste, touch and hearing, respectively, rather than sight as is the case for sensory sets 20 and 30. Alternatively, any corresponding combination of sensory stimuli of smell, taste, texture, sound and sight might be used together as the set of sensory stimuli. The only constraints are that each sensory stimuli should correspond to one, and only one, archetype, and that the relationship between each sensory stimuli and the archetype should not be known or immediately apparent to individuals taking the self-test.

Figure 4:
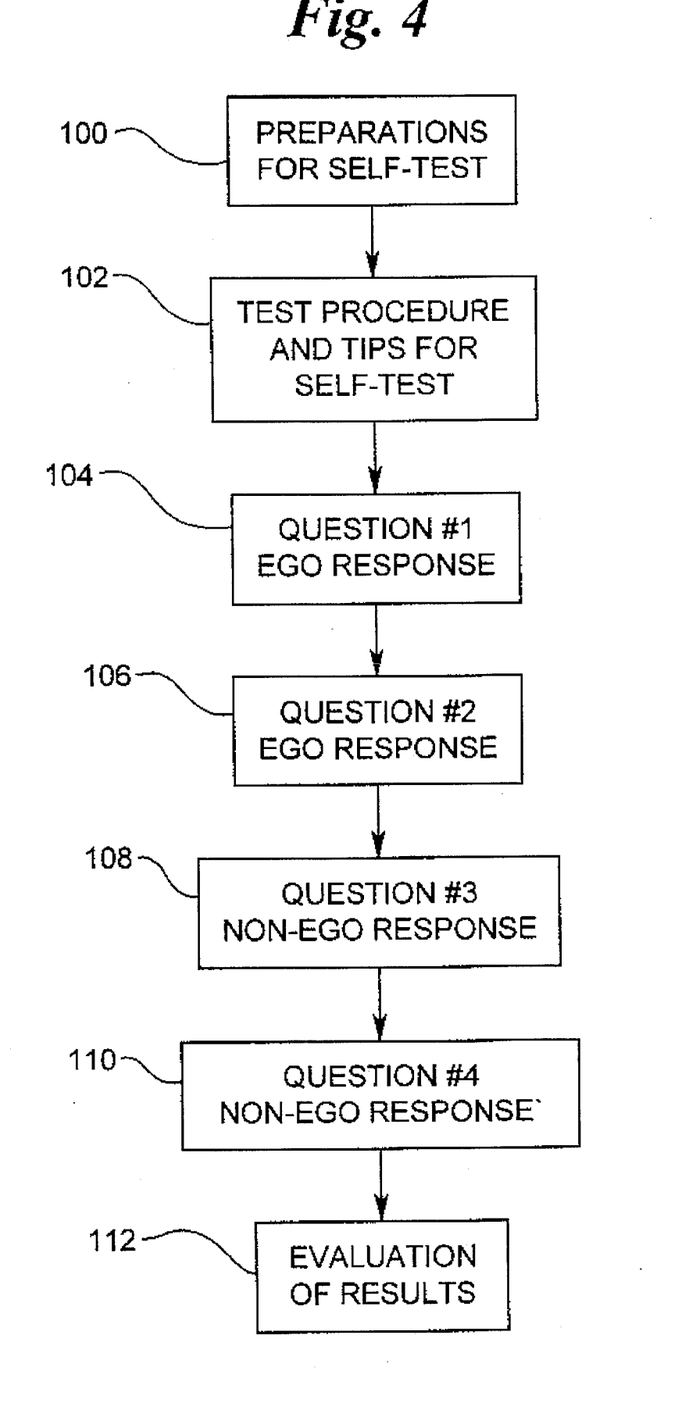
FIG. 4 is a flow chart detailing the procedural flow of a preferred embodiment of the self-typing system of the present invention.

Referring now to FIG. 4, a flow chart of a preferred method of performing the self-test system 10 in accordance with the present invention will now be described.

At step 100, individual 14 is instructed from a set of instructional materials 40 (as shown in FIG. 1) regarding preparations for taking self-test 10. Ideally, self test 10 is taken when individual 14 has enough time to be undisturbed and unpressured for about 10–15 minutes. Preferably, a room with full natural light is chosen with no one else present in the room with individual 14. A large mirror in front of which individual 14 can stand and observe him or her self is needed. To prevent distraction, individual 14 preferably is instructed to wear a white or off-white shirt, to pull his or her hair back away from the face, and to remove any makeup, including lipstick, blush or eyeliner. Eyeglasses or colored contact lenses may interfere with self test 10, so, if possible, individual 14 is instructed to remove these when asked to look at his or her image in the mirror.

At step 102, the procedure for self test 10 is described and several tips in taking self test 10 are presented. In a preferred embodiment, a response sheet is used to record the response of individual 14 to the various stimuli of sets 20, 30 for four questions. It is helpful to instruct individual 14 to "go with his or her first impulse and not change answers." It will be apparent that self test 10 does not have one "right" answer for everyone. In addition, it is helpful to advise individual 14 as to what is not being sought by the questions asked in self test 10. In the case of the shapes of set 20, for example, it is helpful to indicate that what is not being sought is "the shape that stands out the most; the shape that is a contrast to your features; the shape that is a match to your features; the shape that represents some ideal of beauty for you; or psychological or metaphysical meanings associated with the shapes."

At step 104, individual 14 is instructed with regard to a first question. In the case of set 20, for example, individual 14 would be instructed to take the shapes out of a sealed envelope and place the shapes with the printed side face down. Individual 14 is instructed that, in addition to shape, it should be noted that each shape has a unique texture and color. To put individual 14 at ease and allow for the most natural sensory perceptions to be observed, individual 14 is instructed to relax and take several deep breaths before answering each question. In this case, the question asked in 104 might be a comparison of likes based on an ego response to the stimuli of set 20, such as "WHICH ONE ARE YOU DRAWN TO?". Individual 14 is then instructed to indicate his or her response on a response sheet 42 (as shown in FIG. 1).

At step 106, individual 14 is instructed with regard to a second question. In the example of the shapes of set 20, individual 14 would be instructed to pick up each shape briefly, for 2 or 3 seconds. Again, a question based on an ego response of a comparison of like might be asked, such as "WHICH ONE FEELS BEST TO YOU?". Again, individual 14 is instructed to indicate his or her response on response sheet 42.

At step 108, individual 14 is instructed with regard to a third question. In this example, the third question is designed to evoke a comparison of harmonization of each of the at least four sensory stimuli 22, 24, 26 and 28 with individual 14 based on a non-ego response to each of the stimuli. Individual 14 is instructed to stand in front of the mirror and pretend they are looking at someone they do not know. While looking in the mirror, individual 14 is instructed to pick up one shape at a time using the same hand throughout, and, first hold the shape below the face at chin level, then hold the shape on the right side of the face beside the check. To facilitate this process, stimuli 22, 24, 26 and 28 preferably have directional arrows printed on a back side and individual 14 is instructed to hold the shapes in the direction indicated by the arrows on the back of the shape so that they cannot see the arrows when looking in the mirror. After taking a couple of deep breaths, individual 14 is asked to respond to a question such as "WHICH ONE LOOKS THE MOST HARMONIOUS WITH THE IMAGE YOU SEE?". This response is then indicated on response sheet 42.

At step 110, individual 14 is instructed with respect to a fourth question. In the case of the shapes of set 20, and to access a non-ego response, individual 14 might be asked to imagine that he or she had to sit next to each shape for a very long time. With this image in mind, individual 14 would then be asked a question like "WHICH ONE WOULD BE THE MOST COMFORTABLE FOR YOU TO BE WITH FOR THE LONGEST TIME?". The response to this question would be indicated on response sheet 42.

At step 112, individual 14 would be directed to a second and separate set of instructional materials 44 (as shown in FIG. 1) for instructions on how to interpret the results of self test 10 which have been indicated on the Response Sheet. It will be appreciated that both sets of instructional materials 40 and 44 may be presented to individual 14 as written material, video material, audio material, or any combination thereof. Instructional materials 44 would indicate for the first time to individual 14, the relationship between stimuli 22, 24, 26 and 28 and each of the corresponding archetype representing essence 12 of that individual 14. In addition, individual 14 would be instructed as to which one of the four questions was the non-placebo question. Alternatively, individual 14 may be instructed by materials 44 to compare two or more response on response sheet 42 to confirm the selection of the correct archetype representing essence 12 of that individual 14.

In an alternate embodiment of the present invention, individual 14 would be asked to repeat steps 104–110 using a second set 30 of stimuli and, possibly, a second set of instruction materials 40, before advancing to step 112. As with the use of two non-placebo questions, the use of a second set 30 of stimuli would be for the purpose of confirming the sensory stimuli corresponding to essence 12 which was selected by individual 14. In the case of the stimuli arrangement shown in FIG. 3, for example, the non-placebo questions asked of individual 14 may include one or more of the following: "Please observe the wheel, turning the wheel to each of the four categories, observe for only 1–2 seconds. Which one of the four categories could you be around the longest?"; "If you were visiting a home with these colors and designs in these categories, which would you be the most comfortable in?"; or "If you could decorating one room, your private room in which to relax in your home, which category would you pick to decorate that room?"

I claim:

1. A method for self-typing of an inherent characteristic archetype that is an essence of an individual comprising the steps of:
   (a) providing the individual with at least four sensory stimuli, each sensory stimuli having a relation with only one of at least four characteristic archetypes, the relation between each sensory stimuli and its characteristic archetype being unknown to the individual;
   (b) having the individual observe at least one perception in response to a sensory reaction for each of the at least four sensory stimuli; and
   (c) based upon the perceptions of step (b), selecting one of the at least four sensory stimuli as the inherent characteristic archetype that represents the essence of the individual.

2. The method of claim 1 wherein step (b) comprises the sub-steps of:
   (b1) observing a first perception in response to a sensory reaction for each of the at least four sensory stimuli, the first perception being evoked in response to a first question posed to the individual; and
   (b2) repeating the sensory reaction for each of the at least four sensory stimuli and observing at least a second perception, the second perception being evoked in response to at least a second question posed to the individual, wherein at least one of the questions posed to the individual is a placebo question and the perception observed in response to the placebo question is not used in step (c).

3. The method of claim 2 wherein the first question in step (b1) evokes a comparison of likes of each of the at least four sensory stimuli by the individual based on an ego response to each of the at least four sensory stimuli and wherein one of the at least second questions in step (b2) evokes a comparison of harmonization of each of the at least four sensory stimuli with the individual based on a non-ego response to each of the at least four sensory stimuli.

4. The method of claim 2 wherein the questions of steps (b1) and (b2) are posed to the individual in a format selected from the set comprising: written material, video material, audio material, or any combination thereof.

5. The method of claim 1 further comprising the step of:
   (d) confirming the one of the at least four sensory stimuli selected as the inherent characteristic archetype by repeating steps (a)–(c) with at least one different set of at least four sensory stimuli.

6. The method of claim 1 wherein the sensory stimuli of step (a) are selected from the set comprising: a smell, a taste, a sound, a shape, a pattern, a texture, a color, or any combination thereof.

7. The method of claim 1 wherein the sensory stimuli are four forms, each form having a unique shape, a unique color, and a unique surface texture and wherein the sensory reaction in step (b) is a visual comparison of each form with the individual.

8. The method of claim 1 wherein the sensory stimuli are four scents, each scent having a unique smell and wherein the sensory reaction in step (b) is a comparison of each scent.

9. The method of claim 1 wherein the sensory stimuli are four sample tastes, each sample taste having a unique taste and smell and wherein the sensory reaction in step (b) is a comparison of each sample taste.

10. The method of claim 1 wherein the sensory stimuli are four sample sounds, each sample sound having a combination of tone and wherein the sensory reaction in step (b) is a comparison of each sample sound.

11. The method of claim 1 wherein the sensory stimuli are four harmonic family sets, each harmonic family sets having a series of sample representations, each sample representation having a unique color, a unique design and a unique texture and all of the sample representations for each set presenting a harmonic family of visually perceived energetic patterns that is associated with only one of at least four characteristic archetypes, and wherein the sensory reaction in step (b) is a visual comparison of each harmonic family set with the individual.

12. A system for self-typing an inherent characteristic archetype that is an essence of an individual comprising:
   at least four sensory stimuli, each sensory stimuli having a relation with only one of at least four characteristic archetypes, the relation between each sensory stimuli and its characteristic archetype being unknown to the individual; and instruction means for directing the individual to observe at least one perception in response to a sensory reaction for each of the at least four sensory stimuli and, in response, select one of the at least four sensory stimuli as the inherent characteristic archetype representing the essence of the individual.

13. The system of claim 12 wherein the instruction means further comprise means for posing a first question to the individual to observe a first perception in response to a sensory reaction for each of the at least four sensory stimuli; and means for posing at least a second question to the individual to observe at least a second perception after repeating the sensory reaction for each of the at least four sensory stimuli, wherein at least one of the questions posed to the individual is a placebo question and the perception observed in response to the placebo question is not used to select the inherent characteristic archetype of the individual.

14. The system of claim 13 wherein the first question evokes a comparison of likes of each of the at least four sensory stimuli by the individual based on an ego response to each of the at least four sensory stimuli and wherein one of the at least second questions evokes a comparison of harmonization of each of the at least four sensory stimuli with the individual based on a non-ego response to each of the at least four sensory stimuli.

15. The system of claim 12 wherein the at least four sensory stimuli are comprised of at least two different sets of at least four sensory stimuli and wherein the instruction means directs the individual to observe at least one perception in response to a sensory reaction for each different set and to compare the inherent characteristic archetypes selected for each different set.

16. The system of claim 12 wherein the instruction means is presented to the individual in a format selected from the set comprising: written material, video material, audio material, or any combination thereof.

17. The system of claim 12 wherein the sensory stimuli are selected from the set comprising: a smell, a taste, a sound, a shape, a pattern, a texture, a color, or any combination thereof.

18. The system of claim 12 wherein the sensory stimuli are four indicia, each indicia having a unique shape, a unique color, and a unique surface texture and wherein the sensory reaction is a visual comparison of each indicia with the individual.

19. The system of claim 12 wherein the sensory stimuli are four scents, each scent having a unique smell and wherein the sensory reaction is a comparison of each scent.

20. The system of claim 12 wherein the sensory stimuli are four sample tastes, each sample taste having a unique taste and smell and wherein the sensory reaction is a comparison of each sample taste.

21. The system of claim 12 wherein the sensory stimuli are four sample sounds, each sample sound having a combination of tone and wherein the sensory reaction is a comparison of each sample sound.

22. The system of claim 12 wherein the sensory stimuli are four harmonic family sets, each harmonic family set having a series of sample representations, each sample representation having a unique color, a unique design and a unique texture and all of the sample representations for each set presenting a harmonic family of visually perceived energetic patterns that are associated with only one of at least four characteristic archetypes, and wherein the sensory reaction is a visual comparison of each harmonic family set with the individual.

23. A set of four sensory stimuli for use in typing an inherent characteristic archetype that is an essence of an individual comprising:

a first sensory stimuli comprised of a circular shape having a surface texture that is natural and semi-gloss and a color tint that is a pale yellow;

a second sensory stimuli comprised of a tear-drop shape having a surface texture that is smooth and velvety and a color tint that is a pale rose;

a third sensory stimuli comprised of a triangular shape having a surface texture that is rough and course and a color tint that is a pale brown; and a fourth sensory stimuli comprised of an oval shape having a surface texture that is hard, glossy and shiny and a color tint that is a pure white, all of the sensory stimuli being of a size that may hand-held.

24. The set of four sensory stimuli of claim 23 wherein each stimuli constructed from materials selected from the set comprising: solely from paperboard stock matching the desired physical characteristics, or from pieces of fabric material matching the desired physical characteristics that are adhered to a rigid backing.

25. An arrangement of a set of four sensory stimuli for use in typing an inherent characteristic archetype that is an essence of an individual comprising:

four groups or family of swatches of both color and designs, including:

a first family of vibrant color swatches having light, curved, chaotic and upward-directed designs;

a second family of muted color swatches having smooth, curved, flowing and downward-directed designs;

a third family of earth-tone color swatches having staccato, straight, asymmetric and upward-directed designs; and a fourth family of intense color swatches having still, straight or curved, symmetric and downward-directed designs.

26. The arrangement of claim 25 wherein the arrangement is selected from the set comprising: a circular arrangement wherein each of the four families are presented as color swatches within a unique quarter circle or a circular shape, or a strip arrangement wherein each of the four families are presented as individual strips of color swatches.

\* \* \* \* \*